US006956022B2

(12) United States Patent
Tamura et al.

(10) Patent No.: US 6,956,022 B2
(45) Date of Patent: Oct. 18, 2005

(54) AGENTS FOR PREVENTING AND TREATING THROMBOCYTOPENIA

(75) Inventors: Masahiko Tamura, Shizuoka-ken (JP); Yasuhiro Oda, Nagano-ken (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 156 days.

(21) Appl. No.: 10/026,696

(22) Filed: Dec. 27, 2001

(65) Prior Publication Data

US 2002/0058626 A1 May 16, 2002

Related U.S. Application Data

(62) Division of application No. 09/117,379, filed as application No. PCT/JP97/00255 on Feb. 3, 1997, now Pat. No. 6,342,477.

(30) Foreign Application Priority Data

Feb. 1, 1996 (JP) ......................................... 1996/16701

(51) Int. Cl.$^7$ ........................ A61K 38/00; A61K 38/29; C07K 16/00
(52) U.S. Cl. ............................. 514/2; 514/12; 514/802; 514/834; 530/380; 530/381; 530/397; 530/399
(58) Field of Search ............................. 514/2, 12, 802, 514/834; 530/380, 381, 397, 399

(56) References Cited

U.S. PATENT DOCUMENTS

| 3,886,132 A | 5/1975 | Brewer ........................ 474/177 |
| 4,692,433 A | 9/1987 | Hostetler et al. .............. 514/12 |

FOREIGN PATENT DOCUMENTS

| EP | 0 748 817 A | 12/1996 |
| WO | WO 92 00753 A | 1/1992 |
| WO | WO 93 06845 A | 4/1993 |

OTHER PUBLICATIONS

Benigni, et al; "Inhibition of Human Platelet Aggregation by Parathyroid Hormone"; *Am. J. Nephrol*, 5:243–247 (1985).
Brickman et al; "Parathyroid Hormone, Platelet Calcium, and Blood Pressure in Normotensive Subjects"; *Hypertension*, vol. 18, No. 2, pp. 176–182, 1991.
Stedmann's Medical Dictionary, 26$^{th}$ Ed.; M. Spraycar, editor, William & Wilkins, Baltimore, 1995.
Meytes,et al; "Effect of Parathyroid Hormone on Erythropoiesis"; *J. Clin. Invest*. 67:1263–1269; 1981.
Hokom et al; "Pegylated Megakaryocyte Growth and Development Factor Abrogates the Lethal Thrombocytopenia Associated with Carboplatin and Irradiation in Mice"; *Blood*, 86: No. 12, 4486–4492, 1995.
Herodin et al; "Recombinant Glycosylated Human Interleukin-6 Accelerates Peripheral Blood Platelet Count Recovery in Radiation–Induced Bone Marrow Depression in Baboons"; *Blood*, vol. 80, No. 3, pp. 688–695; 1992.
Wallace et al; "Thrombocytopoletic Properties of Oncostatin M"; *Blood*; vol. 86, No. 4, pp. 1310–1315; 1995.
Leonard et al; "Recombinant Human Interleukin-11 Stimulates Multilineage Hematopoietic Recovery in Mice After a Myelosuppressive Regimen of Sublethal Irradiation and Carboplatin"; *Blood*; vol. 83, No. 6; pp. 1499–1506; 1994.
Shivdasani et al; "Transcription Factor NF–E2 is Required for Platelet Formation Independent of the Actions of Thrombopoietin MGDF in Megakaryocyte Development"; *Cell*; vol. 81, pp. 695–704, 1995.

*Primary Examiner*—Jon Weber
*Assistant Examiner*—Abdel A. Mohamed
(74) *Attorney, Agent, or Firm*—Browdy and Neimark, PLLC

(57) ABSTRACT

Method of increasing blood platelet formation by administering a parathyroid hormone (PTH) or at least one PTH derivative as an active ingredient.

11 Claims, 4 Drawing Sheets

US 6,956,022 B2

AGENTS FOR PREVENTING AND TREATING THROMBOCYTOPENIA

This is a division of parent application Ser. No. 09/117,379, filed Jul. 29, 1998, now U.S. Pat. No. 6,342,477, the national stage under 35 U.S.C. §371 of international application PCT/JP97/00255, filed Feb. 3, 1997 which designated the United States, was nationalized Jul. 29, 1998, and was not published in English.

FIELD OF INVENTION

This invention relates to agents for preventing and treating thrombocytopenia that contain a parathyroid hormone (PTH) or a derivative thereof as an active ingredient.

BACKGROUND OF INVENTION

Platelets, as well as erythrocytes and neutrophils which are also in the class of mature corpuscles, originate from hematopoietic stem cells and are produced by the differentiation and proliferation of these cells. In the early stage of the hematopoietic process, hematopoietic stem cells differentiate and proliferate to megakaryocytes via their precursor cells. Mature magakaryocytes form proplatelets which would eventually be released into peripheral blood as platelets. It has been found that various hematopoietic factors and cytokines are involved in the series of steps in the above-described platelet production process. For example, it has been shown experimentally that interleukin-3 is involved in the stage from stem cells to megakaryocytes, interleukin-6 in the maturing of megakaryocytes and thrombopoietin in the stage from stem cells to the maturing of megakacyocytes. It is speculated that a certain factor is also involved in the process of platelet production and release from mature magakacyocytes but no such factors are yet to be identified.

Thrombocytopenia manifests itself if either one of the steps in the above-described thrombopoietic process is interfered with and there are two major causes of such interference, abnormality in hematopoietic cells and abnormality in hematopoietic factors. In the first case, the differentiation and proliferation of hematopoietic cells are interfered with by either congenital or acquired causes. Aplastic anemia and osteomyelodysplasia syndrome are known to occur by congenital causes and bone marrow transplantation and the administration of chemotherapeutics are two known acquired causes. As for the abnormality in hematopoietic factors, cyclic thrombocytopenia is known to be caused by this reason.

Transfusion of platelets is currently considered to be an effective means of treating thrombocytopenia but this treatment does not necessarily supply an adequate amount of platelets and, in addition, it involves the risk of infection with viruses and other pathogens. Therefore, the development of agents effective in preventing and treating thrombocytopenia is desired.

A parathyroid hormone (PTH) is known as one of the important hormones for bone metabolism. Numerous reports have so far been published to describe the actions of PTH on the bone but there are few reports on its action on the hematopoietic system. The exception is the report by Meytes et al (J. Clin. Invest. Vol. 67, 1263–1269:1981), which showed that PTH interfered with the in vitro colony formation by BFU-E (precursor cells of erythrocytes) and CFU-GM (precursor cells of granulocytes and macrophages). Thus, nothing has been unraveled about the action of PTH on thrombopoiesis.

SUMMARY OF INVENTION

An object of the present invention is to provide agents for preventing and treating thrombocytopenia. Another object of the invention is to provide pharmaceutical drugs that are effective in treating or preventing diseases that accompany thrombocytopenia.

As the result of their intensive studies, the present inventors found that a parathyroid hormone (PTH) or its derivatives are effective in the treatment of thrombocytopenia, and the present invention has been accomplished on the basis of this finding.

Thus, the present invention relates essentially to an agent for preventing and treating thrombocytopenia that contains a parathyroid hormone (PTH) or a derivative thereof as an active ingredient. The invention also relates to an agent for preventing and treating thrombocytopenia that contains human PTH(1–84) or one or more derivatives thereof as an active ingredient. The invention further relates to an agent for preventing and treating thrombocytopenia that contains a parathyroid hormone (PTH) or human PTH(1–34) as an active ingredient. The invention also relates to an agent for preventing and treating thrombocytopenia that contains a parathyroid hormone (PTH) as an active ingredient. The invention further relates to an agent for preventing and treating thrombocytopenia that contains human PTH(1–84) as an active ingredient. The invention also relates to an agent for preventing and treating thrombocytopenia that contains a derivative of parathyroid hormone (PTH) as an active ingredient. The invention further relates to an agent for preventing and treating thrombocytopenia that contains human PTH(1–34) as an active ingredient. It should be noted that aside from thrombocytopenia, the agents of the invention for preventing and treating thrombocytopenia are intended to prevent and treat various diseases that are attributable to thrombocytopenia such as thrombocytopenic purpura and various diseases that tend to cause bleeding due to, presumably, thrombocytopenia.

DETAILED DESCRIPTION OF EMBODIMENTS

Figure 1:
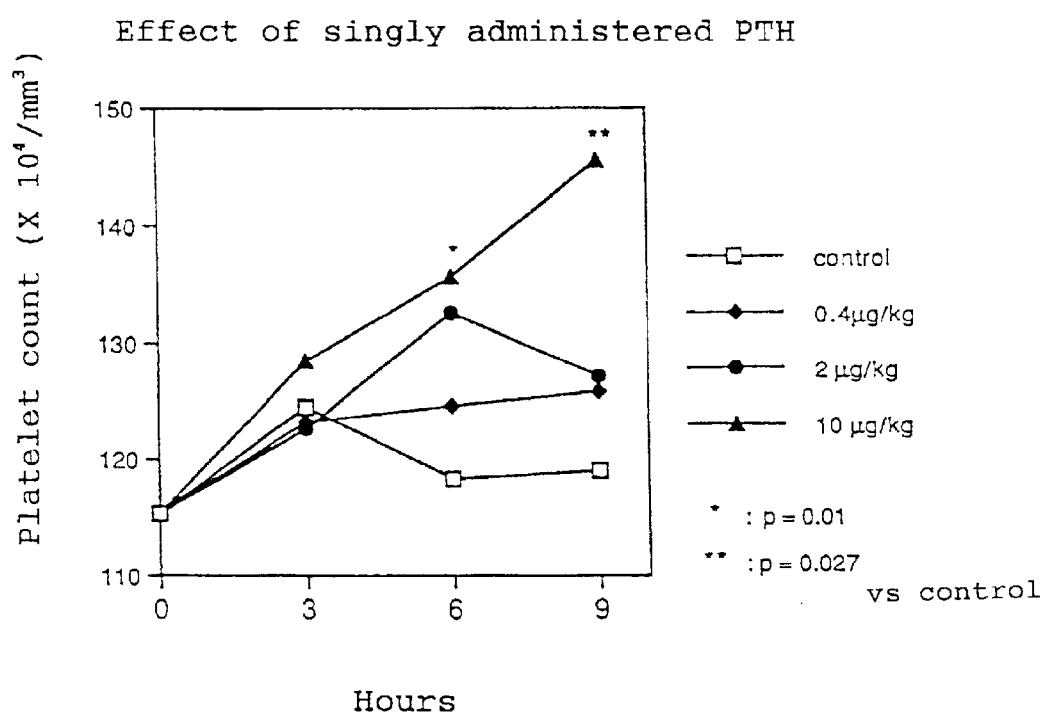
FIG. 1 is a graph showing the platelet increasing action of PTH (when administered in a single dose to mouse)

The parathyroid hormone (PTH) to be used in the invention may occur in various forms including PTH of a native type, PTH produced by genetic engineering techniques and PTH synthesized chemically; preferably it refers to human PTH(1–84) composed of 84 amino acid residues. Examples of PTH derivatives include partial peptides of the PTH as defined above, the constituent amino acids of the PTH per se of partial peptides thereof which are partly replaced by other amino acids, the constituent amino acids of the PTH per se or partial peptides thereof which are partly depleted, as well as peptides that have at least amino acid added to the PTH per se or partial peptides thereof; the peptides as PTH derivatives should have similar activities to the PTH itself. Exemplary partial peptides of PTH include human PTH (1–34), human PTH(1–64), human PTH(35–84) and bovine PTH(1–34). PTH(1–34) refers to a partial peptide of PTH that is composed of 34 amino acids as counted from the N terminus of PTH.

Preferred examples of amino acid replacement include substitution of leucine or norleucine for the constituent amino acid in the 8-position, substitution of leucine or norleucine for the constituent amino acid in the 18-position, and substitution of tyrosine for the constituent amino acid in the 34-position.

Preferred examples of the parathyroid hormone (PTH) or its derivatives which are to be used as agents for preventing and treating thrombocytopenia in the invention include human PTH(1–84), human PTH(1–34), human PTH(1–38), human PTH(1–37), human PTH(1–34)–$NH_2$ and so forth; more preferred examples include human PTH(1–84) and human PTH(134); the most preferred is human PTH(1–84).

The agents for preventing and treating thrombocytopenia refer to the therapeutics and preventives, preferably therapeutics, of thrombocytopenia, thrombocytopenic purpura and various diseases that tend to cause bleeding due, presumably, to thrombocytopenia. Conditions included in the scope of thrombocytopenia are the disease caused by radiation therapy and the disease accompanying bone marrow transplantation. Also included in the scope of thrombocytopenia are the disease caused by the selective suppression of megakaryocytes due, for example, to pharmaceutical drugs (phenylbutazone, gold compounds, tolbutamide and chemotherapeutics) and viral infection, the diseases caused by systemic myelocytic deficiencies such as aplastic anemia, autoimmune thrombocytopenic purpura, osteomyelodysplasis syndrome, leukemia, multiple myeloma and megakaryoblastic anemia, drug-induced immune thrombocytopenia, post-transfusion purpura and secondary immune thrombocytopenia.

A typical dosage form for the pharmaceutical drugs of the invention is as an injection (e.g. liquid preparations and lyophilized preparations) that is produced by ordinary pharmaceutical formulation procedures applicable to peptides; also useful are dosage forms that are intended to be show local and delayed actions, as by inclusion within microcapsules or incorporation in sheets of gel. When formulating pharmaceutical preparations, pharmaceutically acceptable adjuvants may be added. In order to increase the half-time in blood, pharmaceutical preparations modified with polyethylene glycol may be formulated.

Useful adjuvants include base materials, stabilizers, antiseptics, preservatives, emulsifiers, suspending agents, solubilizers, solvent promoters, lubricants, flavoring agents, coloring agents, fragrances, soothing agents, vehicles, binders, viscous agents, buffers, etc. Specific examples include calcium carbonate, lactose, sucrose, sorbitol, mannitol, starches, amylopectin, cellulosic derivatives, gelatin, cacao butter, distilled water for injections, aqueous sodium chloride, Ringer's solution, glucose solution, human serum albumin and so forth.

When preparing the pharmaceutical drugs of the invention using the above-mentioned adjuvants, suitable adjuvants may be selected with reference to a certain data book such as "A List of Pharmacoutical Additives" (published by the Committee on Medical Laws and Regulations, Tokyo Society of Pharmaceutical Industry, Foundation and by the Study Committee on Medical Laws and Regulations, Osaka Society of Pharmaceutical Industry, Foundation). The amounts in which the adjuvants are to be used my be selected as appropriate for the dosage form and other factors from within the ranges tolerated by pharmaceutical formulation procedures.

The pharmaceutical drugs of the invention may be administered by either systemic or local route, preferably by a local route such as subcutaneously, intravenously, intranasally or transpulmonarily. In principle, the duration of administration should not be shorter than the period over which the patient is clinically diagnosed as suffering from thrombocytopenia; depending on the etiology of the disease, the clinical physician may decide to continue the administration after the patient's recovery. If the occurrence of thrombocytopenia is anticipated as in the case where a chemotherapeutic is being administered, the drugs of the invention may be administered for preventive purposes even if the patient is not currently suffering from disease. The frequency of administration may range from Once a month to daily administration; preferably, the frequency ranges from once in two weeks to about five times a week or, alternatively, the drugs may be administered daily.

The dose of the PTH of the invention varies with the disease it is indicated for, the severity of the disease and other factors; for systemic administration, the PTH's dose ranges from about 1 $\mu$g to about 1000 $\mu$g per kg of body weight, preferably from 5 $\mu$g to 200 $\mu$g per kg of body weight.

EXAMPLES

The present invention will now be described in greater detail with reference to the following examples. The human PTH(1–84) used in Examples 1–4 was prepared by an improved version of the methods described in Japanese Domestic Announcement (kohyo) No. 505259/1992 and J. Biol. Chem., 265, 15854(1990). The human PTH(1–34) used in Example 3 was purchased from Peptide Institute, Inc.

Example 1

Test for Single-dose Administration to Mouse
(Animal on Experiment)
Nine-week old male C57B1/6N mice as purchased from Japan Charles River Co. Ltd. were used in the experiment.
(Preparation of Drug Solutions to be Administered)
Human PTH(1–84) was dissolved in a citrate buffer (pH 5; containing 0.05% of Tween 80) at final concentrations of 1, 0.2 and 0.04 ~g/mL so as to prepare the drug solutions to be administered.
(Administration)
Each of the thus prepared drug solutions and a control (citrate buffer) was administered to 15 mice through the tail vein in a volume of 10 mL/kg. Hence, the dose of the human PTH(1–84) was 0, 0.4, 2 and 10 $\mu$g/kg, respectively. The administration was initiated at 10 a.m.
(Blood Sampling and Counting Peripheral Corpuscle)
After 3, 6 and 9 hours of the administration, five mice were picked up at random from each group of animals and blood samples were withdrawn through the orbital vein. At 10 a.m. on the same day, separate blood samples were taken from untreated mice (four in number) to obtain the preadministration value. Peripheral corpuscle counts were obtained with an automatic corpuscle counter F-800 (TOA MEDICAL ELECTRONICS CO., LTD.)
(Results)
The results are shown in FIG. 1. The group administered with 10 $\mu$g/kg of PTH showed a significant increase in platelet counts over the control at 6 and 9 h after the administration. Thus, the platelet count increased within a short period after the administration of PTH.

Example 2

Test for Daily Administration to Mouse
(Animal on Experiment)
Nine-week old male C57B1/6N mice as purchased from Japan Charles River Co., Ltd. were used in the experiment.

(Preparation of Drug Solutions to be Administered)

Drug solutions to be administered were prepared basically by the same procedure as in Example 1 to give drug concentrations of 5, 20 and 80 μg/mL.

(Administration)

The mice under test were divided into four groups, which were administered subcutaneously with the three drug solutions and a control (citrate buffer) once a day in a volume of 10 mL/kg. Hence, the dose of the drug was 0, 50, 200 and 800 μg/kg, respectively. The administration was initiated at 10 a.m.

(Blood Sampling and Counting Peripheral Corpuscles)

On days 5, 7 and 9 after the start of administration, five or six mice were picked up at random from each group of animals and blood samples were withdrawn through the orbital vein. The sampling of blood was timed to occur 24 h of the final administration. Separate blood samples were taken from untreated mice (five in number) to obtain the value for normal mouse. Peripheral corpuscle counts were obtained with an automatic corpuscle counter F-800(TOA MEDICAL ELECTRONICS CO., LTD.).

(Results)

Figure 2:
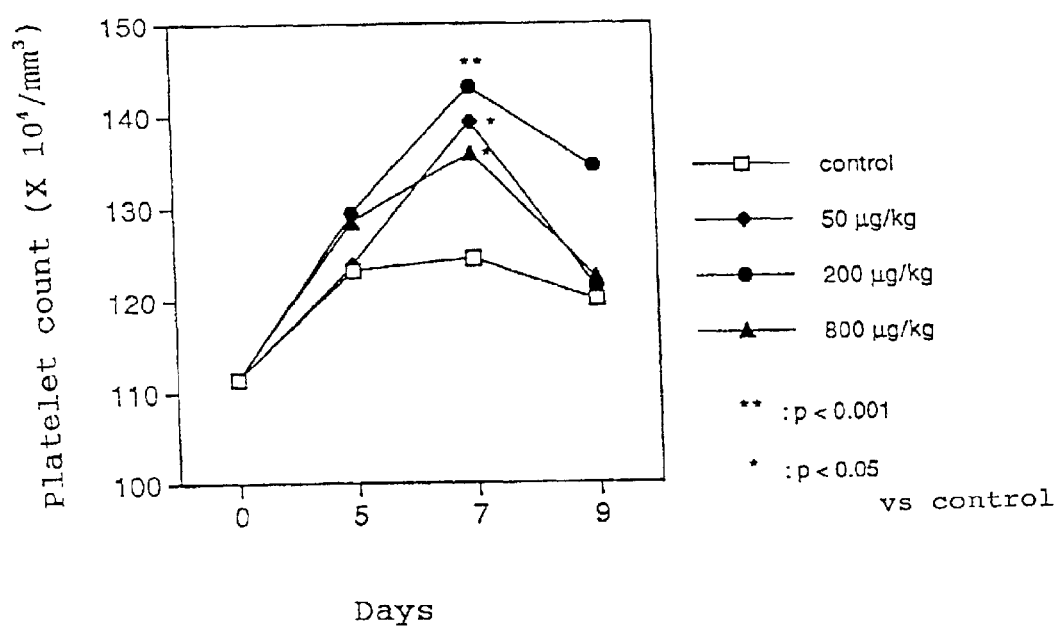
FIG. 2 is a graph showing the platelet increasing action of PTH (when administered daily to mouse)

The results are shown in FIG. 2. On day 5, the platelet count showed a tendency to increase only in the groups administered 200 and 800 μg/kg of PTH but on day 7, all of the treated groups were significantly higher in platelet count than the control. It was therefore clear that the PTH also had a platelet increasing action even when it was administered daily.

Example 3

Effectiveness of PTH Derivative (Animal on Experiment)

Ten-week old male C57B1/6N mice as purchased from Japan Charles River Co., Ltd. were used in the experiment.

(Preparation of Drug Solutions to be Administered)

Drug solutions to be administered were prepared basically from human PTH(1–84) and human PTH(1–34) by the same procedure as in Example 1 to give a drug concentration of 20 μg/mL.

(Administration)

Eighteen mice were divided into three groups, which were administered subcutaneously with the two drug solutions and a control (citrate buffer) for six days on a once-a-day basis in a volume of 10 mL/kg. Hence, the dose of the drug was 0 and 200 μg/kg, respectively. The administration was initiated at 10 a.m.

(Blood Sampling and Counting Peripheral Corpuscles)

After 24 h of the final administration, a blood sample was withdrawn from each mouse through the orbital vein. Peripheral corpuscle counts were obtained with an automatic corpuscle counter F-800 (TOA MEDICAL ELECTRONICS CO., LTD)

(Result)

Figure 3:
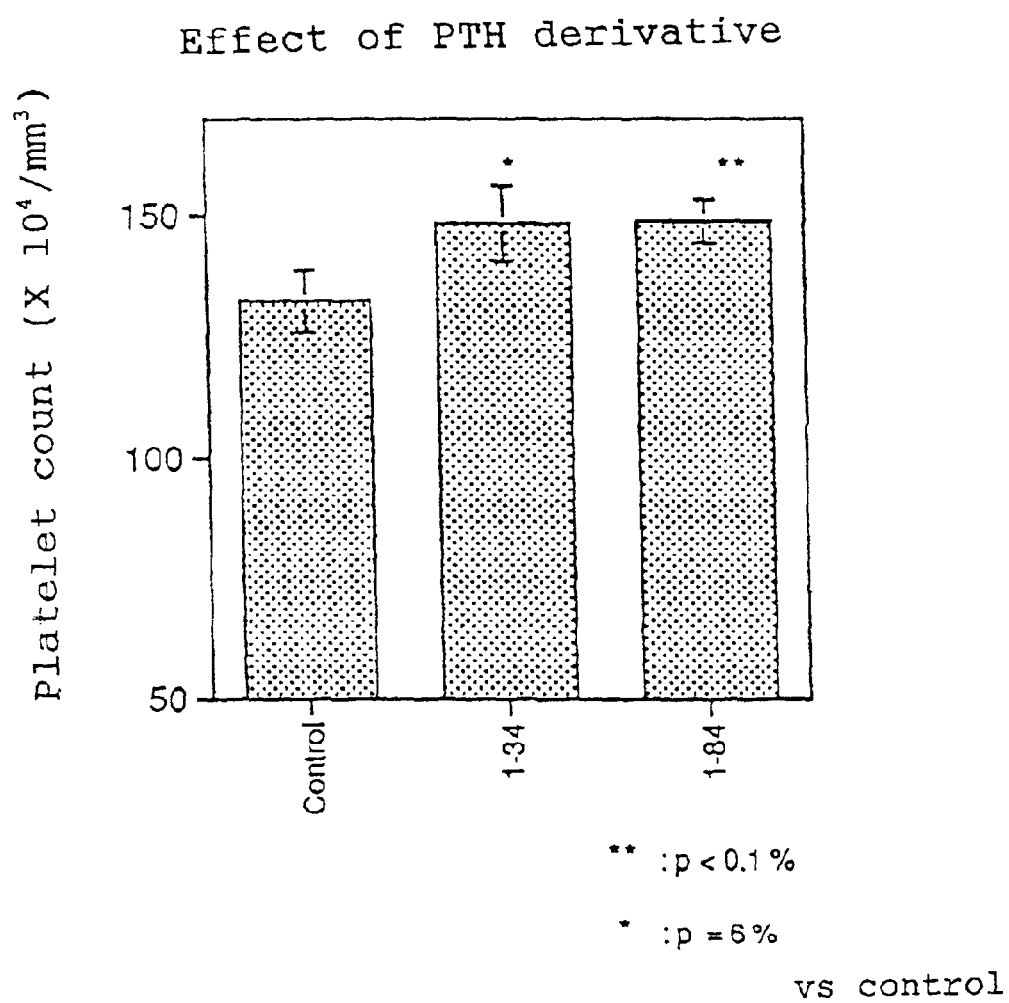
FIG. 3 is a graph showing the platelet increasing action of a PTH derivative (when administered daily to mouse)

The results are shown in FIG. 3. Obviously, PTH(134) has a comparable platelet increasing action to PTH(1–84). From these results, one may well expect that even shorter partial peptides of PTH as well as partial peptides of intermediate sizes, for example, PTH(35–84) and PTH(1–64) would have similar actions.

Example 4

Test for Daily Administration to Rabbit

Animal on Experiment)

Six 12–15 week old male Japanese albino rabbits JW/CSK were used in the experiment. The animals were individually kept in aluminum rabbit bracket cages Rb-1 ($350^w \times 500^d \times 350^h$ mm) in a vavarium in a specific pathogen-free environment under the following conditions: temperature, 24±2° C.; humidity, 50±10%; illumination, light turned on at 5:00 and turned off at 19:00; ventilation, 15 changes/hr. Each animal was supplied with 120 g of a radiation-sterilized feed for rabbits RM (purchased from Funahashi Farm) per day. The animals were also allowed to drink to tap water ad libitum from an automatic water feeder.

(Preparation of Drug Solutions to be Administered)

Human PTH(1–84) was administered in a volume of 2 mL/vial at a concentration of 200 μg/mL. A solvent was also supplied in a volume of 2 mL/vial. Both the drug and the control were stored at −135° C. until use.

(Method of Administration)

PTH (200 μg/kg) was administered to the rabbits subcutaneously at the back of their neck for 13 consecutive days. The solvent was similarly administered in the same volume as the dose of a rh-PTH solution calculated from their body weight.

(Blood Sampling and Counting Peripheral Corpuscles)

Blood samples (0.5 mL) were withdrawn from the rabbits through the lateral auricular vein before the administration and on days 2, 6, 9 and 13 during the administration period. Each blood sample was distributed among blood testing vessels SB-41S (TOA MEDICAL ELECTRONICS CO., LTD.) and heparinized; thereafter, platelet counts were obtained with an automatic corpuscle counter F-800 (TOA MEDICAL ELECTRONICS CO. LTD.).

(Results)

Figure 4:
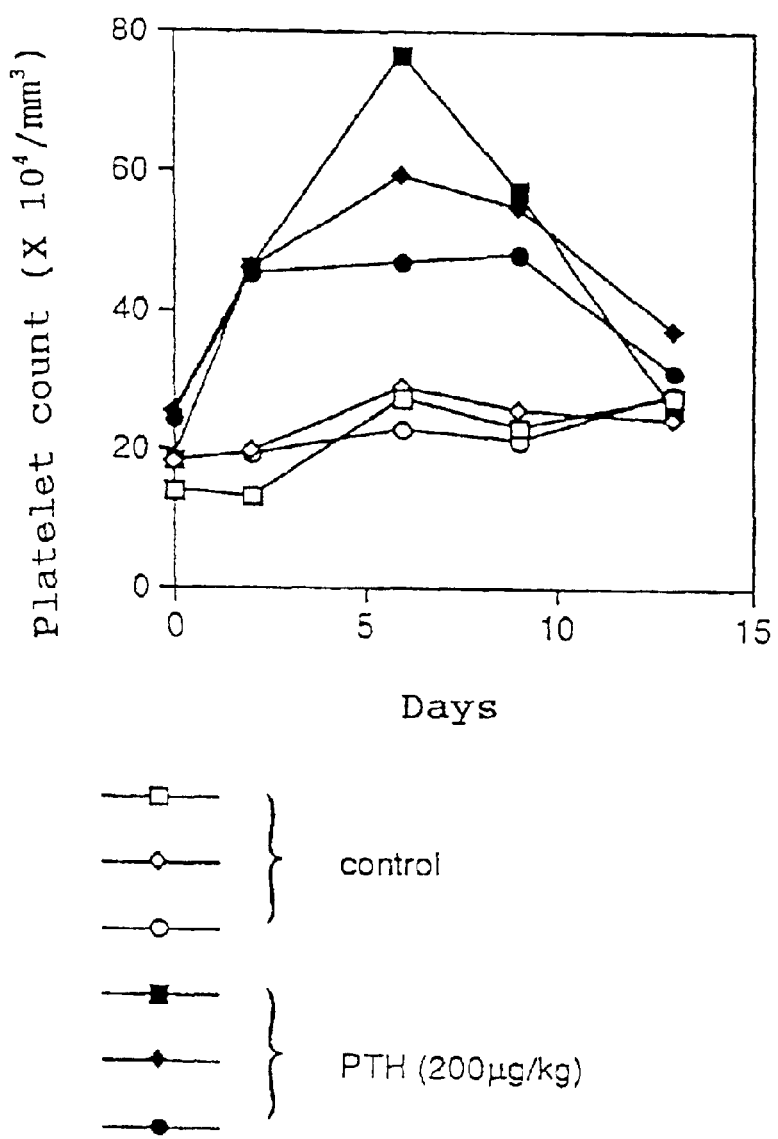
FIG. 4 is a graph showing the platelet increasing action of PTH (when administered daily to rabbit).

Three rabbits were daily administered with 200 μg/kg of PTH and platelets were counted on days 0, 2, 6, 9 and 13 of the administration period. The results are shown in FIG. 4. Starting on day 2 of the administration, the platelet count increased until day 6, exhibiting two to four times as great as the initial value. The platelet count substantially returned to the initial level on day 13.

Industrial Applicability

The agents of the present invention which contain a parathyroid hormone (PTH) or a derivative thereof as an active ingredient are useful as therapeutics and preventives of thrombocytopenia, thrombocytopenic purpura and various diseases that tend to cause bleeding due, presumably, to thrombocytopenia.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A method for increasing platelet count in a patient in need thereof, comprising
   administering to said patient an effective amount of a composition comprising a parathyroid hormone (PTH) or a derivative thereof.

2. The method according to claim 1 wherein said PTH or PTH derivative modified with polyethylene glycol is administered.

3. The method according to claim 1 wherein said PTH or PTH derivative is administered encapsulated within microcapsules.

4. The method according to claim 1 wherein said PTH or PTH derivative is incorporated in a sheet of gel.

5. The method according to claim 1 wherein said effective amount is in the range of 1 μg to 1,000 μg per kg of body weight administered systemically at a frequency ranging from once per day to once per month.

6. The method according to claim 1 wherein said effective amount is from 5 μg to 200 μg per kg of body weight administered from once every two weeks to once daily.

7. The method according to claim 1 wherein the route of said administration is subcutaneously.

8. The method according to claim 1 wherein the route of said administration is intravenously.

9. The method according to claim 1 wherein the route of said administration is intranasally.

10. The method according to claim 1 wherein the route of said administration is transpulmonarily.

11. The method of claim 1, wherein said PTH or PTH derivative is human PTH (1–34).

* * * * *